Figure 1:
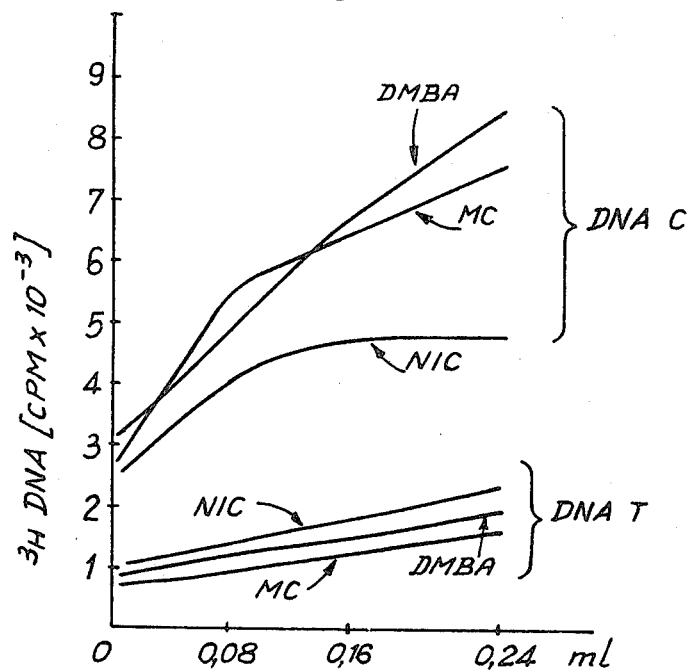

United States Patent [19]

Beljanski

[11] 4,264,729

[45] Apr. 28, 1981

[54] METHOD AND REAGENT FOR DETECTING CANCERIGENIC AND ANTICANCEROUS SUBSTANCES

[76] Inventor: Mirko Beljanski, 46 Boulevard de Port-Royal, 75005 Paris, France

[21] Appl. No.: 943,834

[22] Filed: Sep. 19, 1978

[30] Foreign Application Priority Data

Oct. 4, 1978 [FR] France ............................... 77 28208

[51] Int. Cl.$^3$ .......................... C12Q 1/68; C12Q 1/48
[52] U.S. Cl. .......................................... 435/6; 435/15; 424/1.5
[58] Field of Search .................... 435/6, 15, 29, 32, 4, 435/172; 424/1.5, 2

[56] References Cited

U.S. PATENT DOCUMENTS

| | | | |
|---|---|---|---|
| 3,755,086 | 8/1973 | Heimer | 435/6 |
| 3,798,131 | 3/1974 | Rounds et al. | 435/6 |
| 4,066,510 | 1/1978 | Thilly | 435/172 |
| 4,072,574 | 2/1978 | Loeb et al. | 435/6 |

OTHER PUBLICATIONS

Shirasaka, et al., "Purification of Thymidine Kinase Yoshida Sarcoma by Affinity Chromatography, and DNA Synthesis in Tumor-Bearing Rats.", *Chem. Abstracts*, vol. 83, No. 5, p. 343, (1975), Abs. No. 41213d.

*Primary Examiner*—Thomas G. Wiseman
*Attorney, Agent, or Firm*—Sughrue, Rothwell, Mion, Zinn and Macpeak

[57] ABSTRACT

The effects of a substance on the replication process in vitro of ADN separated from sound tissues (check tissue) on the one hand and of DNA separated from cancerous tissue (cancerous DNA) on the other hand, are being compared. Cancerigenic substances are identified since they stimulate the replication of cancerous DNA more strongly than the replication of check tissue; specifically anticancerous substances since they inhibit the replication of cancerous DNA but not the replication of check tissue, toxic substances since they inhibit the replication of cancerous DNA as well as that of check tissue; and neutral substances since they do not have any effect either on the replication of cancerous DNA or on that of check tissue.

20 Claims, 6 Drawing Figures

METHOD AND REAGENT FOR DETECTING CANCERIGENIC AND ANTICANCEROUS SUBSTANCES

The invention has for its object a method by means of which it is possible in a short period of time, between 1 to 3 hours, to determine the purity of a substance or to identify cancerigenic substances as well as substances having a specifically anticancerous effect and even toxic and neutral substances.

According to the invention, the new method comprises a biological test "in vitro" completely different from the tests provided until now in view of estimating the cancerigenic potential of substances, starting from, for example a mutagenic substance. The test according to the invention makes it possible to foresee the action of a substance on the genome and accordingly the survival of both the sound cell and the cancerous cell.

The test according to the invention is based on the compared actions of the substance to be tested in the replication "in vitro" of desoxyribonucleic acids (DNA) obtained from sound cells on the one hand, and from cancerous (or tumorous) cells on the other hand.

The test according to the invention allows not only to select the substances having a cancerigenic activity and the toxic substances, but in fact such a test allows to separate the tested substances in four groups:

*cancerigenic substances*, which stimulate strongly the replication of DNA separated from cancerous tissues (or cells), and slightly but substantially, the replication of DNA separated from sound tissues (or cells);

*neutral substances*, which have no effect on either the replication of DNA from sound tissues, or on the replication of ADN from cancerous tissues;

*toxic substances*, which, with a concentration equal to that of conventional cancerigenic substances, inhibit the replication of DNA separated as well from sound tissues as from cancerous tissues. Among these substances, many show a cancerigenic power, even when used at low dose;

substances called *"specifically anticancerous"*, which inhibit a little if at all the replication of DNA from sound tissues, whilst they are strong inhibitors for replication of DNA from cancerous tissues.

According to the invention, there is provided a method in which there is observed, in measuring the radioactive acidoprecipitable DNA, the synthesis of DNA on a matrix of DNA separated from sound tissues on the one hand, and on a matrix of DNA separated from cancerous tissues on the other hand, in a medium comprising four desoxyribonucleoside-5'-triphosphates, one of which is radioactive, and one enzyme DNA-polymerase, with the substance to be tested and without it.

For carrying into effect the test, which in itself is very short, it is necessary to hold several preparations, previously and carefully proven, of matricial DNA separated from sound tissues (check tissue, hereinafter referenced to as DNA T) and of matricial DNA separated from cancerous tissues (hereinafter referenced to as DNA C).

The DNA C preparations are obtained by using as raw material various cancerous tissues or tumours taken on a human or animal organ, such as breast, lung, ovary, neuro-carcinome, ascites, etc. It is also possible to use cultures of cancerous cells such as KB or Hela cells, etc.

The preparations of DNA T are obtained in the same manner by using as raw material sound tissues separated from various human or animal organs, or from sound cells cultivated "in vitro" in a suitable medium.

For each test, it is necessary to hold at least four couples of matricial DNA of different origins, each couple being formed by an DNA T preparation and an DNA C preparation originating from the same organ, of the same animal kind. For example, there is used at least four couples selected among the following: DNA T and DNA C separated from lung tissue; DNA T and DNA C separated from breast tissue; DNA T and DNA C separated from ovary tissue; DNA T of primary cells of monkey kidney (RS), or of "Vero" cells, or of "SIRC" cells in culture and DNA C of KB cells or Hela cells, or L cells in culture.

The necessity of carrying out the test on at least four couples of DNA originating from different organs is explained by the fact that some substances which are neutral with respect to an DNA separated from a given organ, are found to be cancerigenic, or on the contrary specifically anticancerous with respect to DNA separated from another organ, or from cells in culture.

Besides, some substances which seem to be specifically anticancerous when they are present with a relatively low concentration in the reactional medium, are found to be toxic with a higher concentration. It is then necessary to carry out the test with a reactional medium containing a scale of concentrations of the substance to be tested, from 0 to 100 µg.

For separating DNA, either from sound tissues or from cancerous tissues, there is used a modified conventional method of separation and purification (J. Narmur, J. Mol. Biol. 3 208, 1961). When a cancerous tissue or a tumour is used, the neighbouring sound or questionable tissues must first be discarded, and reciprocally, the sound tissues must be free from any questionable tissues.

Immediately after exeresis, the tissue is either frozen at $-20°$ C., or finely crushed in a kneading machine, in the presence of a buffer 2 SSC (containing 17.4 g of NaCl and 10.7 g of trisodic citrate for 1 liter of sterile distilled water) in a sterile aqueous solution (1 to 3 ml of buffer according to the volume of tissue) and of a final concentration of 0.2% in laurylsulphate (by adding an aqueous mother solution of laurylsulphate at 20%).

In order to get rid of the proteins and to keep the DNA, several extractions are made in the presence of buffer 2 SSC and phenol (solution containing 10% of water), followed by extractions with chloroform and by centrifugations according to the conventional technique of separation and purification of DNA. The DNA present in the aqueous phases is precipitated in 96° alcohol, picked up with a glass rod, solved in a little volume of 1 SSC, then treated by the pancreatic ribonucleases and $T_1$, what requires a whole supplementary cycle of repurification with phenol, then with chloroform. The DNA is dialysed against a solution of 2 SSC (24 hours at 4° C.), dosed by absorption in ultraviolet and stored frozen at $-20°$ C., several months if necessary. Before use, the DNA is once more dialysed during several hours against sterile distilled water.

The DNA is characterized by its absorbance in ultraviolet at 260 nm and 280 nm. The typical ratio 260/280 varies from 2.0 to 2.1 according to the preparation. The content of the ARN in proteins varies from 0.3 to 0.6% and the content in polyribonucleotids having resisted the action of nucleases and contaminating the DNA is between 1 and 3%. The RNA (ribonucleic acid) can be eliminated by degradation by KOH 0.3 M (final concentration) during 16 hours at 36° C., and the DNA is then dialysed and stored as hereinabove mentioned.

A preparation of DNA-polymerase is also necessary to carry out the test.

Since polymerases DNA separated from mammalians synthetise DNA through a mechanism identical to that used by polymerase-DNA I of Escherichia coli, it is possible to use a polymerase DNA depending DNA, and preferably polymerase ADN I, separated and partially purified starting from extracts of E. coli M 500 Sho-R and from wild E. coli T 3000. The enzyme must be passed twice successively on a column DEAE cellulose, according to the method described, so as to provide a ratio of 280/260 in the range of 1.5 to 1.8 (M. PLAWECKI and M. BELJANSKI, C.R. Acad. Sci. Paris, 278, serie D, 1974, p. 1413 and M. BELJANSKI and col., C.R. Acad. Sci. Paris, 280, serie D, 1975, p. 363).

The reactional medium, or incubation medium in which is observed the DNA replication in presence of the substance to be tested comprises, for 0.15 ml (final volume):

0.5 to 1 μg of matricial DNA (DNA T or DNA C)
4 desoxyribonucleoside-5'-triphosphates (5 nanomoles each)
25 μM of buffer tris-HCl (pH exactly 7.65)
0 to 100 μg of substance to be tested
2 μg of Mg Cl$_2$
40 to 80 μg of ADN-polymerase enzyme, added after all the other components of the medium.

The four desoxyribonucleoside-5'-triphosphates comprise:
desoxyguanosine-5'-triphosphate,
desoxycytidine-5'-triphosphate,
desoxyadenosine-5'-triphosphate,
thymidine-5'-triphosphate, one of which being radioactive ($^3$H or $^{14}$C; 50,000 strokes per minute). As radioactive compound, the (methyl-$^3$H)thymidine-5'-triphosphate is preferably used.

The concentration in the medium of the substance to be tested may be comprised between 0 and 100 μg, because some substances can be cancerigenic in a very diluted solution, and toxic in higher concentrations.

The test is to be carried out, then, with a scale of concentrations, beginning by low concentrations of the substance to be tested.

The incubation is carried out during 10 minutes at 36° C., and the reaction is stopped by adding trichloracetic acid (ATC) at 5%.

Without delay, the precipitate, formed by the synthetised radioactive DNA is filtered on glass millipores, washed with 5% ATC, dried, and the radioactivity is determined in a Packard spectrometer (scintillation counter), the sample dipping in the liquid suitable for the counter.

So have been comparatively studied the synthesis in-vitro of DNA on matrices of check DNA and cancerous DNA in presence of various chemical substances, known as having cancerigenic properties:
the 3-methyl-cholantrene (MC)
nicotine (NIC)
9,10-dimethyl-1,2-benzanthracene (DMBA)
benzo (a) pyrene
4-benzenesulfonamido-5 nitrobenzene (DCBN)
an asbestos sample, etc.

FIG. 1 shows curves plotted for the first three compounds listed above (MC, NIC and DMBA), plotting in the ordinate the amount of radioactive DNA $^3$H synthetised (strokes per minute) in presence of DNA-T and DNA-C, as a function of the amount of substance to be tested in the reactional medium.

These curves show that each of the tested substances stimulates the replication of DNA, but the stimulation is clearly stronger for cancerous DNA than for check DNA.

Similar results have been obtained for all the cancerous substances tested.

Some cancerous substances, especially the dyestuffs, such as acridine orange, must be tested with very low concentrations, since with high concentrations, they are toxic and inhibit as well the replication of check DNA as that of cancerous DNA.

Figure 2:
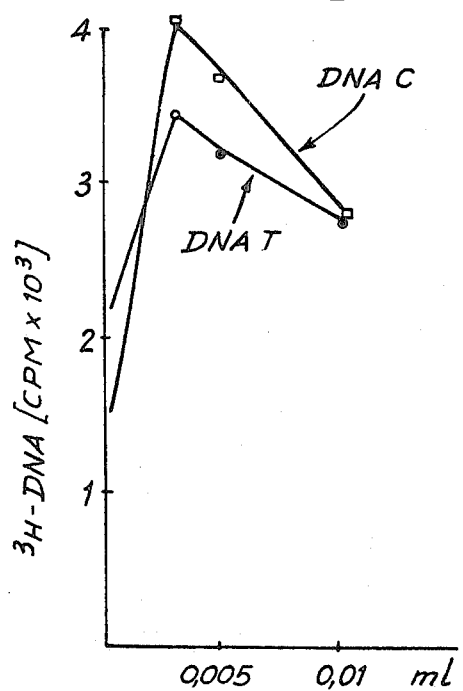

FIG. 2 shows curves obtained with acridine orange, in the same conditions as for FIG. 1. This figure shows that with 0.005 ml acridine orange (0.1 mg/ml) in the medium, the stimulation of DNA-C replication is clearly stronger than that of DNA-T, but between 0,005 and 0,01 ml of acridine orange in the medium, this substance slows down the synthesis, as well of DNA-C as that of DNA-T.

A second group of substances, so-called "neutral substances" have no effect, nor stimulating, nor inhibiting on the replication of DNA-T, nor on that of DNA-C.

Figure 3:
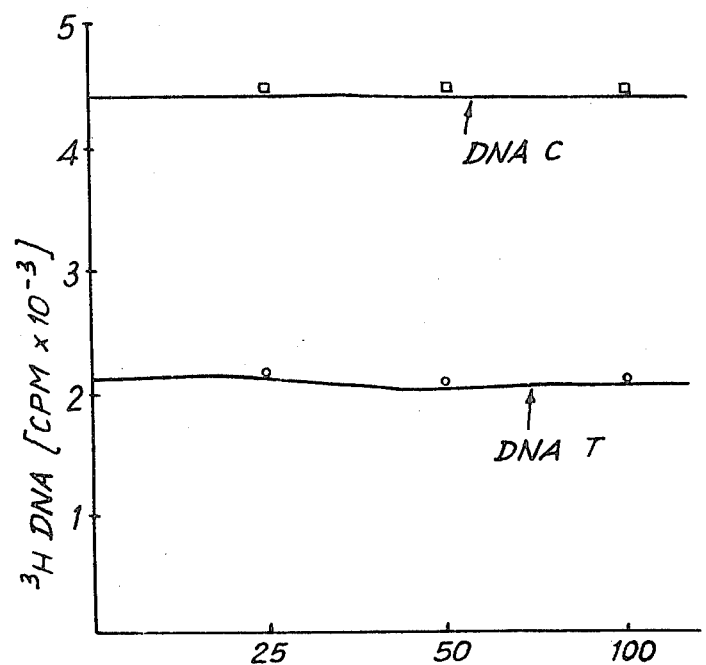

FIG. 3 shows curves obtained in similar conditions as for obtaining FIG. 1, with a neutral substance called "Xabar", which is a combination of reserpiline nicotinate, theophylline and papaverine. Nicotinic acid and piperazine are to be grouped among these neutral substances.

Figure 6:
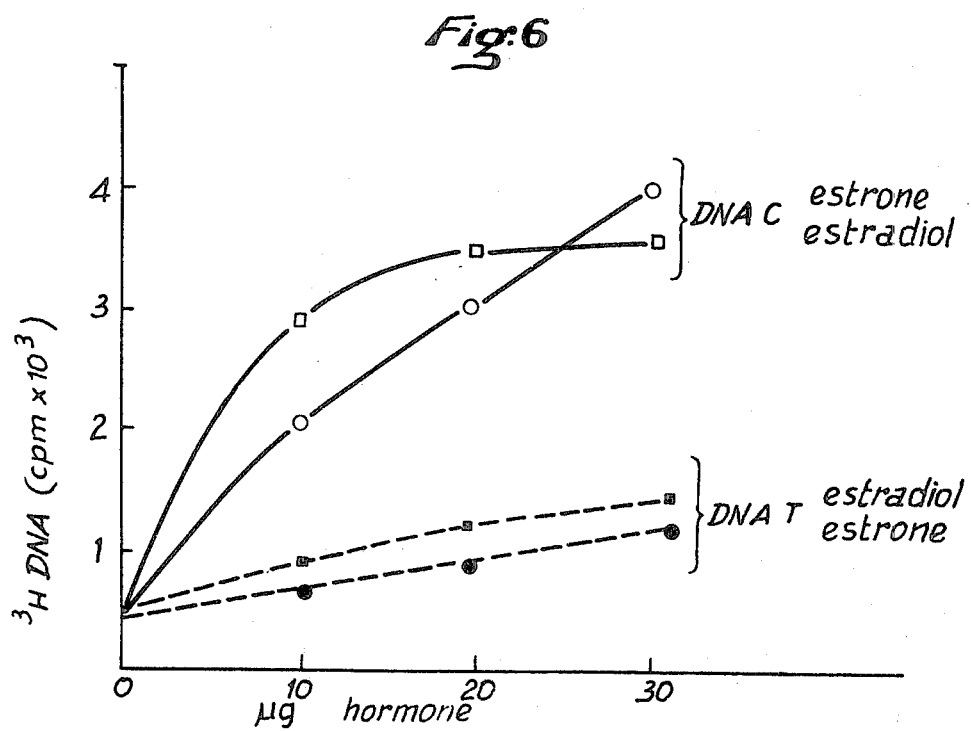

FIG. 6 shows the curves obtained in similar conditions as for obtaining FIG. 1, using various genital hormones (estrone and estradiol) with the concentrations given on FIG. 6. Estrone and estradiol stimulate weakly the replication of DNA-T separated from sound breast tissues, and very strongly the replication of DNA-C separated from cancerous breast tissues. Similar results have been observed with ovary DNA. On the contrary, genital hormones have no effect on the replication of DNA taken on check and cancerous tissues such as lung or liver tissues.

The very great reaction sensitivity of sound and cancerous DNA replication also makes the test sensitive to substances which are simply toxic. In presence of toxic substances at low concentrations, an inhibition of replication of sound DNA is observed, as well as inhibition of replication of cancerous DNA, essentially through enzymatic activity inhibition.

Figure 4:
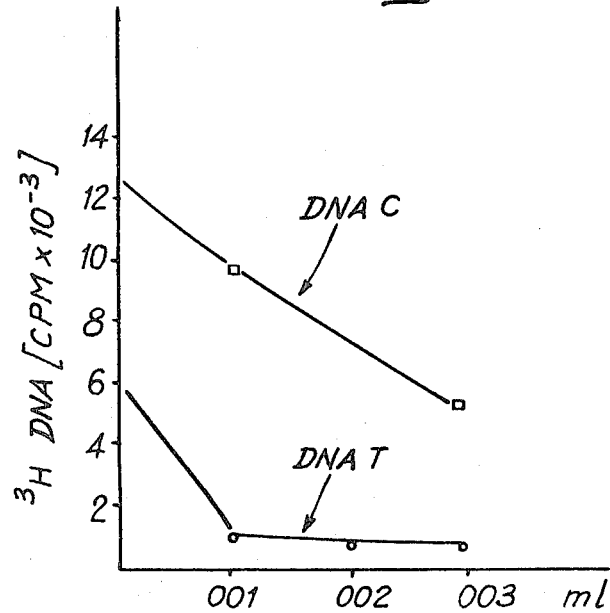

FIG. 4 illustrates this inhibition non selective for the Diquat (ethylene-1,1-bipyridilium-2,2-dibromid).

Finally, the method of the invention insensitive to the substances having specifically anticancerous properties. These substances inhibit the replication, the initiation of cancerous substances, or the elongation (or both) of the DNA chain in course of synthesis when these substances are in presence of cancerous DNA. On the contrary, they should have little or no effect at all on the DNA-T replication.

Figure 5:
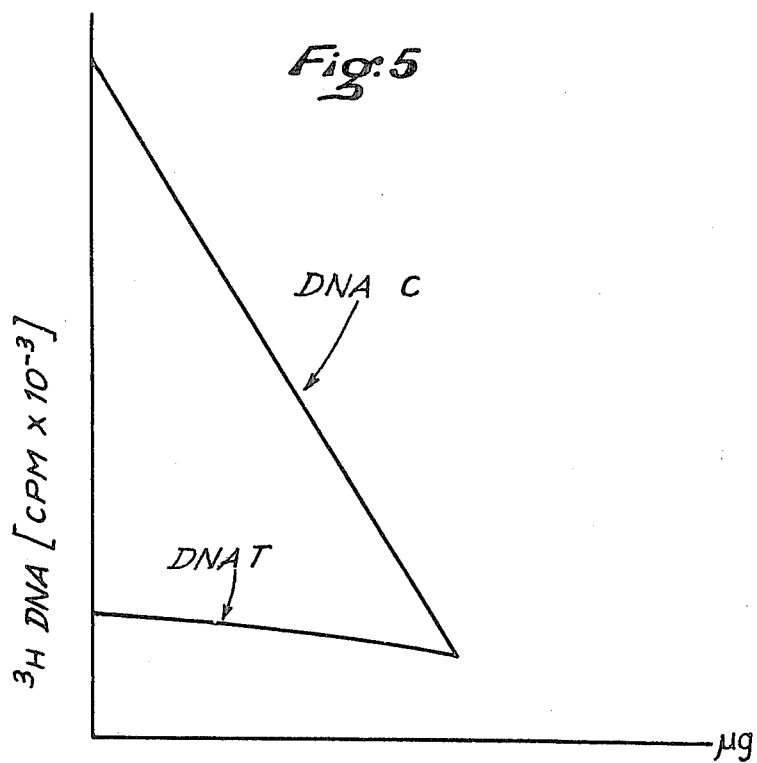

The feature, and theoretical definition of a specifically anticancerous substance is to differentiate cancerous and sound tissues, then to destroy the first and not the other. With the method according to the invention, there are grouped in the "specifically anticancerous" category the substances able to differentiate the DNA of cancerous origin from the DNA of not cancerous origin, and able to inhibit the replication of the first without inhibiting the replication of the other. According to the invention, the theoretical curve of a specifically anticancerous substance (i.e. inhibiting only the replication of DNA-C) will have the form shown on FIG. 5.

The test of the invention so allows to select the substances according to the action they cause, comparatively on the replication of check DNA and that of cancerous DNA.

The test of the invention allows essentially to find out, on the one hand, substances having a cancerigenic influence, and on the other hand substances having a "specifically anticancerous" activity, and can so help to carry out a first sorting out before starting the pharmacological study in the research of new anticancerous drugs.

What I claim is:

1. A method for determining the purity of a substance or detecting if a substance is a cancerigenic substance, an anticancerous substance, a toxic substance, or a neutral substance comprising comparing the effects of the substance in various concentrations on the replication in vitro of matricial DNA as a check DNA separated from sound tissues or cells wherein a portion of the substance to be tested is placed in the presence of the check DNA in one test, and another portion of the substance to be tested is placed in the presence of the cancerous DNA in a second test and each test is performed in an incubation medium buffered with tris-HCl, having equimolecular amounts of 4 desoxyribonucleoside-5'-triphosphates, one of which is marked with $^{14}C$ or $^{3}H$ in the presence of a DNA-polymerase enzyme, at 36° C. for 10 minutes, trichloracetic acid is added to stop the reaction and the radioactivity of the formed precipitate, constituted by the synthetised DNA, is measured.

2. The method according to claim 1 wherein the effects on the substance to be tested are compared on four different DNA couples, one DNA couple constituted of one check DNA and one cancerous DNA originating from tissues of the same organ of the same animal kind, or from the same group of cultivated cells.

3. The method according to claim 2, wherein the four DNA couples are selected from the group of DNA couples consisting of check DNA and cancerous DNA separated from lung tissues, check DNA and cancerous DNA separated from ovary tissues, check DNA and cancerous DNA separated from breast tissues, check DNA from primary cells of monkey kidneys (RS) or from KB, Hela or L cells.

4. The method according to claim 1 wherein the four desoxyribonucleoside-5'-triphosphates present in the incubation medium are desoxyguanosine-5'-triphosphate, desoxyadenosine-5'-triphosphate, desoxycytidine-5'-triphosphate, and thymidine-5'-triphosphate.

5. The method according to claim 4 wherein the marked desoxyribonucleoside-5'-triphosphate is the (methyl-$^{3}H$) thymidine-5'-triphosphate.

6. The method according to claim 4 wherein the polymerase DNA enzyme used is a polymerase DNA depending-DNA separated from *E. coli* the pH of the reaction being set at 7.65.

7. The method of claim 6 wherein the polymerase DNA enzyme is polymerase-DNA depending-DNA I.

8. The method according to claim 4 wherein a dose of 0 to 100 micrograms of the substance to be tested is used for 0.5 to 1 micrograms of matricial DNA.

9. The method according to claim 4 wherein the DNA couples are characterized by an absorbance ratio in the UV spectrum at 260 nm and 280 nm of 2.0 and 2.1 respectively and wherein protein content of the DNA couples ranges from 0.3 to 0.6 percent.

10. The method according to claim 1 wherein the marked desoxyribonucleoside-5'-triphosphate is the (methyl-$^{3}H$) thymidine-5'-triphosphate.

11. The method according to claim 10 wherein the polymerase DNA enzyme used is a polymerase-DNA depending-DNA separated from *E. coli* the pH of the reaction be set at 7.65.

12. The method of claim 11 wherein the polymerase DNA enzyme is polymerase-DNA depending-DNA I.

13. The method according to claim 10 wherein a dose of 0 to 100 micrograms of the substance to be tested is used for 0.5 to 1 micrograms of matricial DNA.

14. The method according to claim 10 wherein the DNA couples are characterized by an absorbance ratio in the UV spectrum at 260 nm and 280 nm of 2.0 and 2.1 respectively and wherein protein content in the DNA couples ranges from 0.3 to 0.6 percent.

15. The method according to claim 1 wherein the polymerase DNA enzyme used is a polymerase-DNA depending-DNA depending-DNA I, the pH of the reaction being set at 7.65.

16. The method according to claim 15 wherein the DNA couples are characterized by an absorbance ratio in the UV spectrum at 260 nm and 280 nm of 2.0 and 2.1 respectively and wherein protein content in the DNA couples ranges from 0.3 to 0.6 percent.

17. The method according to claim 15 wherein a dose of 0 to 100 micrograms of the substance to be tested is used for 0.5 to 1 micrograms of matricial DNA.

18. The method according to any one of claims 1, 2 or 3 wherein a dose of 0 to 100 micrograms of the substance to be tested is used for 0.5 to 1 micrograms matricial DNA.

19. The method according to claim 18 wherein the DNA couples are characterized by an absorbance ratio in the UV spectrum at 260 nm and 280 nm of 2.0 and 2.1 respectively and wherein protein content in the DNA couples ranges from 0.3 to 0.6 percent.

20. The method according to claim 1 wherein the DNA couples are characterized by an absorbance ratio in the UV spectrum at 260 nm and 280 nm of 2.0 and 2.1 respectively and wherein protein content in the DNA couples ranges from 0.3 to 0.6 percent.

* * * * *